(12) United States Patent　(10) Patent No.: US 11,861,838 B1
Gardella et al.　(45) Date of Patent: Jan. 2, 2024

(54) SYSTEMS AND METHODS FOR SYSTEM AGNOSTIC AUTOMATED DETECTION OF CARDIOVASCULAR ANOMALIES AND/OR OTHER FEATURES

(71) Applicant: BrightHeart SAS, Paris (FR)

(72) Inventors: Christophe Gardella, Paris (FR); Valentin Thorey, Paris (FR); Eric Askinazi, Paris (FR)

(73) Assignee: BrightHeart SAS, Paris (FR)

( * ) Notice: Subject to any disclaimer, the term of this patent is extended or adjusted under 35 U.S.C. 154(b) by 0 days.

(21) Appl. No.: 18/330,819

(22) Filed: Jun. 7, 2023

(51) Int. Cl.
　*G06K 9/00*　(2022.01)
　*G06T 7/00*　(2017.01)
　(Continued)

(52) U.S. Cl.
　CPC .......... *G06T 7/0014* (2013.01); *A61B 8/0883* (2013.01); *A61B 8/5223* (2013.01);
　(Continued)

(58) Field of Classification Search
　CPC ..................... G06T 7/0014; G06T 5/50; G06T 2207/10016; G06T 2207/20081;
　(Continued)

(56) References Cited

U.S. PATENT DOCUMENTS

| 7,672,491 B2 | 3/2010 | Krishnan et al. |
| 11,478,222 B2 | 10/2022 | Shiran et al. |

(Continued)

FOREIGN PATENT DOCUMENTS

| CN | 114469176 A | * | 5/2022 |
| CN | 114677754 A | * | 6/2022 |

(Continued)

OTHER PUBLICATIONS

Activity recognition, Wikipedia The Free Encyclopedia, retrieved from the internet URL: https://en.wikipedia.org/wiki/Activity_recognition, 12 pages (2018).

(Continued)

*Primary Examiner* — Xin Jia
(74) *Attorney, Agent, or Firm* — Eversheds Sutherland (US) LLP; Christopher C. Bolten; Robert D. Ward

(57) ABSTRACT

Systems and methods are provided for processing image data generated by a medical imaging system such as an ultrasound or echocardiogram system using artificial intelligence and machine learning to determine a presence of one or more congenital heart defects (CHDs) and/or other cardiovascular anomalies in the image data in a manner that is agnostic to the type of imaging system, software, and/or hardware. Image data from various types imaging systems, software, and/or hardware, having various styles of imaging data generated may be processed to determine image styles. Input image data for analysis may then be processed together with representative styles of image data to generate styled input images for each style. The styled input images may be processed by an image analyzer to detect one or more cardiovascular anomalies in the styled image data, for example. Alternatively, training data may be styled and used to train the image analyzer.

30 Claims, 6 Drawing Sheets

(51) Int. Cl.
| | |
|---|---|
| *G06T 5/50* | (2006.01) |
| *G06V 10/762* | (2022.01) |
| *G06V 10/764* | (2022.01) |
| *G06V 10/82* | (2022.01) |
| *G06V 10/774* | (2022.01) |
| *A61B 8/08* | (2006.01) |
| *G16H 50/20* | (2018.01) |

(52) U.S. Cl.
CPC .............. *G06T 5/50* (2013.01); *G06V 10/762* (2022.01); *G06V 10/764* (2022.01); *G06V 10/774* (2022.01); *G06V 10/82* (2022.01); *G16H 50/20* (2018.01); *G06T 2207/10016* (2013.01); *G06T 2207/20081* (2013.01); *G06T 2207/20084* (2013.01); *G06T 2207/30048* (2013.01); *G06T 2207/30101* (2013.01)

(58) Field of Classification Search
CPC . G06T 2207/20084; G06T 2207/30048; G06T 2207/30101; A61B 8/0883; A61B 8/5223; G06V 10/762; G06V 10/764; G06V 10/774; G06V 10/82; G16H 50/20
See application file for complete search history.

(56) References Cited

U.S. PATENT DOCUMENTS

| | | | |
|---|---|---|---|
| 11,488,298 | B2 | 11/2022 | Annangi et al. |
| 11,517,290 | B2 | 12/2022 | Aase et al. |
| 2005/0004465 | A1 | 1/2005 | Abuhamad |
| 2014/0050384 | A1 | 2/2014 | Schmidt et al. |
| 2020/0155114 | A1 | 5/2020 | Park et al. |
| 2020/0214618 | A1 | 7/2020 | Vullings |
| 2020/0345261 | A1 | 11/2020 | Haeusser et al. |
| 2021/0034587 | A1 | 2/2021 | Arye et al. |
| 2021/0150693 | A1 | 5/2021 | Fornwalt et al. |
| 2021/0319558 | A1* | 10/2021 | Min ........................ A61B 5/742 |
| 2021/0345987 | A1 | 11/2021 | Ciofolo-Veit et al. |
| 2022/0012875 | A1 | 1/2022 | Arnaout |
| 2022/0142609 | A1 | 5/2022 | Yeo et al. |
| 2022/0361799 | A1 | 11/2022 | Hong et al. |
| 2023/0064623 | A1 | 3/2023 | Krishnan et al. |
| 2023/0135046 | A1 | 5/2023 | Liu et al. |

FOREIGN PATENT DOCUMENTS

| | | |
|---|---|---|
| CN | 115424335 A * | 12/2022 |
| EP | 3964136 A1 | 3/2022 |

OTHER PUBLICATIONS

Alom, et al., The History Began from AlexNet: A Comprehensive Survey on Deep Learning Approaches, retrieved from the internet URL: https://arxiv.org/abs/1803.01164, 39 pages (2018).
Arnaout, et al., An Ensemble of Neural Networks Provides Expert-Level Prenatal Detection of Complex Congenital Heart Disease, *Nature Medicine*, 27(5):882-891 (May 2021).
Carreira, et al., Quo Vadis, Action Recognition? A New Model and the Kinetics Dataset, retrieved from the internet URL: https://arxiv.org/abs/1705.07750, 10 pages (2018).
Carvalho, et al., ISUOG Practice Guidelines (updated): sonorgraphic screening examination of the fetal heart, Ultrasound Obstet. Gynecol., 41:348-359 (2013).
Cluster, Construct Clusters from Gaussian Mixture Distribution, retrieved from the internet URL: https://www.mathworks.com/help/stats/gmdistribution.cluster.html, 6 pages, retrieved on Apr. 13, 2023.
Cluster Gaussian Mixture Data Using Hard Clustering, retrieved from the internet URL: https://www.mathworks.com/help/stats/cluster-data-from-mixture-of-gaussian-distributions.html, retrieved on Apr. 13, 2023, 6 pages.
Cluster Gaussian Mixture Data Using Soft Clustering, retrieved from the internet URL: https://www.mathworks.com/help/stats/cluster-gaussian-mixture-data-using-soft-clustering.html, retrieved on Apr. 13, 2023, 5 pages.
Create Gaussian Mixture Model, retrieved from the internet URL: https://www.mathworks.com/help/stats/gmdistribution.html#mw_132ef7d2-0aa5-498f-bd6e-824f3edc8567, retrieved on Apr. 13, 2023, 8 pages.
Data Sets, UCF101-Action Recognition Data Set, UCF Center for Research in Computer Vision, 6 pages (2012).
Day, et al., Artificial Intelligence, Fetal Echocardiograhy, and Congenital Heart Disease, Prenatal Diagnosis, 41(6):733-42 (May 2021).
Donofrio, et al., Diagnosis and Treatment of Fetal Cardiac Disease, A Scientific Statement From the American Heart Association, *Circulation*, 129(21):2183-242 (May 2014).
Feichtenhofer, et al., Convolutional Two-Stream Network F'usion for Video Action Recognition, retrieved from the internet URL: https://arxiv.org/abs/1604.06573, 9 pages (2016).
Feichtenhofer, et al., Slow Fast Networks fmr Video Recognition, retrieved from the internet URL: hhttps://arxiv.org/abs/1812.03982, 10 pages (2019).
Feichtenhofer, et al., Spatiotemporal Residual Networks for Video Action Recognition, retrieved from the internet URL: https://arxiv.org/abs/1611.02155, 9 pages (2016).
Fitgmdist, Fit Gaussian Mixture Model to Data, MATLAB fitgmdist, retrieved from the internet URL: https://www.mathworks.com/help/stats/fitgmdist.html, retrieved on Apr. 13, 2023, 17 pages.
Gao, et al., Fast Video Multi-Style Transfer, IEEE Winter Conference on Applications of Computer Vision (WACV), pp. 3222-3230 (2020).
Gatys, et al., A Neural Algorithm of Artistic Style, retrieved from the internet URL: https://arxiv.org/abs/1508.06576, 16 pages (2015).
Gkioxari, et al., Finding Action Tubes, retrieved from internet URL: https://arxiv.org/abs/1411.6031, 10 pages (Nov. 2014).
Goodale, et al., Separate Visual Pathways for Perception and Action, Trends in Neurosciences, 15(1):20-25 (Jan. 1992).
Grandjean, et al., The performance of routine ultrasonographic screening of pregnancies in the Eurofetus Study, *American Journal of Obstetrics and Gynecology*, 181(2):446-454 (Aug. 1999).
He, et al., Deep Residual Learning for Image Recognition, In Proceedings of the IEEE Conference on Computer Vision and Pattern Recognition, pp. 770-778 (2016).
HMDB: A Large Human Motion Database, Serre Lab, retrieved from the internet URL: https://serre-lab.clps.brown.edu/resource/hmdb-a-large-human-motion-database/, accessed on Mar. 23, 2023, 6 pages.
Howard, et al., Improving Ultrasound Video Classification: an Evaluation of Novel Deep Learning Methods in Echocardiography, Journal of Medical Artificial Intelligence, 14 pages (Mar. 2020).
Huang, Real-Time Neural Style Transfer for Videos, IEEE Conference on Computer Vision and Pattern Recognition (CVPR), 9 pages (2017).
Image Gradient, Wikipedia The Free Encyclopedia, retrieved from the internet URL: https://en.wikipedia.org/wiki/Image_gradient, accessed on Mar. 23, 2023, 3 pages.
Ioffe, et al., Batch Normalization: Accelerating Deep Network Training by Reducing Internal Covariate Shift, retrieved from internet URL: https://arxiv.org/abs/1502.03167, 11 pages (2015).
Ji, et al., 3D Convolutional Neural Networks for Human Action Recognition, IEEE Transactions on Pattern Analysis and Machine Intelligence, 35(1), 8 pages (Jan. 2013).
Krizhevsky, et al., ImageNet Classification with Deep Convolutional Neural Networks, Communications of the ACM, 60(6):84-90 (Jun. 2017).
Levy, et al., Fetal Echocardiography: 5-4-3-2-1, The Levy-Stos Method, Gynecologie Obstetrique Pratique, No. 309 (Nov. 2018) (w-English Translation).
Liu, et al., Generalize Ultrasound Image Segmentation via Instant and Plug & Play Style Transfer, retrieved from internet URL: https://arxiv.org/abs/2101.03711, 5 pages (2021).
Liu, et al., Remove Appearance Shift for Ultrasound Image Segmentation via Fast and Universal Style Transfer, retrieved from internet URL: https://arxiv.org/abs/2002.05844, 6 pages (2020).

(56) References Cited

OTHER PUBLICATIONS

Optical flow, Wikipedia The Free Encyclopedia, retrieved from the internet URL: https://en.wikipedia.org/wiki/Optical_flow, accessed on Mar. 23, 2023, 6 pages.

Ouyang, et al., Interpretable AI for Beat-to-Beat Cardiac Function Assessment, Stanford University, 23 pages (2019).

Pan, et al., An Improved Two-stream Inflated 3D ConvNet for Abnormal Behavior Detection, Intelligent Automation and Soft Computing, 29(3):673-688 (Jan. 2021).

Qiu, et al., Learning Spatio-Temporal Representation with Pseudo-3D Residual Networks, retrieved from the internet URL: https://arxiv.org/abs/1711.10305, 9 pages (2017).

Ruder, et al., Artistic Style Transfer for Videos and Spherical Images, International Journal of Computer Vision, 19 pages (2018).

Simonyan, Two-Stream Convolutional Network for Action Recognition in Videos, Visual Geometry Group, University of Oxford, 9 pages (2014).

Simonyan, Very Deep Convolutional Networks for Large-Scale Image Recognition, Visual Geometry Group, University of Oxford, 14 pages (2015).

Sun, et al., Human Action Recognition using Factorized Spatio-Temporal Convolutional Networks, retrieved from the internet URL: https://arxiv.org/abs/1510.00562, 9 pages (2015).

Szegedy, et al., Going Deeper with Convolutions, 2015 IEEE Conference on Computer Vision and Pattern Recognition (CVPR), 9 pages (Jun. 2015).

Szegedy, Going Deeper with Convolutions, IEEE Conference on Computer Vision and Pattern Recognition (CVPR), 12 pages (2014).

Tran, et al., A Closer Look at Spatiotemporal Convolutions for Action Recognition, retrieved from the internet URL: https://arxiv.org/abs/1711.11248, 10 pages (2018).

Tran, et al., Learning Spatiotemporal Features with 3D Convolutional Networks, IEEE International Conference on Computer Vision (ICCV), 16 pages (2015).

Tune Gaussian Mixture Models, retrieved from the internet URL: https://www.mathworks.com/help/stats/tune-gaussian-mixture-models.html, retrieved on Apr. 13, 2023, 7 pages.

Varol, et al., Long-term Temporal Convolutions for Action Recognition, retrieved from the internet URL: https://arxiv.org/abs/1604.04494, 8 pages (2017).

Vivaaindrean, Detection of Robbery-Related Concepts Using Deep Learning, Final Year Project, UTAR, 56 pages (Jan. 2020).

Wang, et al., Actions~Transformations, retrieved from the internet URL: https://arxiv.org/abs/1512.00795, 10 pages (2016).

Wang, et al., Towards Good Practices for Very Deep Two-Stream ConvNets, retrieved from the internet URL: https://arxiv.org/abs/1507.02159, 5 pages (2015).

Wolfe, Deep Learning on Video (Part One): The Early Days, retrieved from the internet URL: https://towardsdatascience.com/deep-learning-on-video-part-one-the-early-days-8a3632ed47d4, 13 pages (2021).

Xie, et al., Rethinking Spatiotemporal Feature Learning: Speed-Accuracy Trade-offs in Video Classification, retrieved from the internet URL: https://arxiv.org/abs/1712.04851, 17 pages (2018).

\* cited by examiner

SYSTEMS AND METHODS FOR SYSTEM AGNOSTIC AUTOMATED DETECTION OF CARDIOVASCULAR ANOMALIES AND/OR OTHER FEATURES

CROSS-REFERENCE TO RELATED APPLICATIONS

This application claims priority to EP Patent Application Serial No. 23305903.9, filed Jun. 7, 2023, the entire contents of which are incorporated herein by reference.

TECHNICAL FIELD

This technology relates, in general, to an image processing system, for example, an image processing system with artificial intelligence and machine learning functionality for detecting cardiovascular anomalies.

BACKGROUND

With today's imaging technology, medical providers may see into a patient's body and may even detect abnormalities and conditions without the need for a surgical procedure. Imaging technology such as ultrasound imaging, for example, permits a medical technician to obtain two and three-dimensional views of a patient's anatomy, such as a patient's heart chambers. For example, echocardiogram uses high frequency sound waves to generate pictures of a patient's heart. Various views may be obtained by manipulating the orientation of the ultrasound sensor with respect to the patient.

Medical imaging may be used by a healthcare provider to perform a medical examination of a patient's anatomy without the need for surgery. For example, a healthcare provider may examine the images generated for visible deviations from normal anatomy. Additionally, a healthcare provider may take measurements using the medical images and may compare the measurements to known normal ranges to identify anomalies.

In one example, a healthcare provider may use echocardiography to identify a heart defect such as ventricular septal defect, which is an abnormal connection between the lower chambers of the heart (i.e., the ventricles). The healthcare provider may visually identify the connection in the medical images and based on the medical images may make a diagnosis. This diagnosis may then lead to surgical intervention or other treatment.

While healthcare providers frequently detect anomalies such as heart defects via medical imaging, defects and various other abnormalities go undetected due to human error, insufficient training, minor visual cues, and various other reasons. This is particularly true with respect to complex anatomy and prenatal imaging. For example, congenital heart defects (CHD) in fetuses are particularly difficult to detect. CHDs during pregnancy are estimated to occur in about one percent of pregnancies. However, between fifty to seventy percent of CHD cases are not properly detected by practitioners. Detection of CHD during pregnancy permits healthcare providers to make a diagnosis and/or promptly provide interventional treatment which could lead to improved fetus and infant health and fewer infant fatalities.

Artificial intelligence and imaging processing systems have been developed to analyze images aid medical practitioners with detecting anomalies and other visual cues in images such as still frames. However, such systems are vulnerable to bias causing inaccurate and/or misleading results. For example, the training sets for such systems may include a large number of anomalies for one type of imaging system (e.g., from a certain brand, model, using a specific sensor or transducer) and may conversely include a large number of normal, unremarkable, images from another type of imaging system.

Due to the unintended bias in the training sets, models trained using this data may associate anomalies with images from one type of imaging system and/or may associate normal images with another type of imaging systems. For example, the image may include a visual arrangement, a logo, and/or other information such as a border, text placement, text size, font, general image style, certain colors, or the like, that is consistently generated by a certain imaging systems. As a result, a model may be trained to associate such style information with anomalies, or conversely normal images. For example, the model may incorrectly determine that an image is normal or abnormal based on the image arrangement and not necessarily the image content generated by the image sensor.

Accordingly, there is a need for improved methods and systems for analyzing and/or processing medical imaging including ultrasound imaging for detecting cardiovascular anomalies such as CHD.

SUMMARY

Provided herein are systems and methods for analyzing a set of medical images that have been styled to include certain style data from multiple types of imaging systems and/or sensors to overcome any bias in a trained image analysis system for determining cardiovascular anomalies such as congenital heart disease (CHD) and optionally for detecting standard views, anatomy key-points, determining measurements, and/or segmentation. The systems and methods may include processing image data generated by multiple imaging systems of different imaging system types to determine style data from image data that may be used to determine representative images for each type of imaging system.

When a new set of images are received from an imaging system, the new set of images and the representative images may be processed by a style transfer generator (e.g., trained network and/or model) to determine several versions of the input set of images each changed to incorporate styles corresponding to the representative style images. The set of styled input images may then be processed by an image analysis system (e.g., anomaly detection model or network), which may be a spatiotemporal neural network, to identify cardiovascular anomalies in the styled set of input images, for example. Alternatively, the image analyzer may be trained using a set of styled images having a standard style. The standard style may be achieved using the style transfer generator.

A method is provided herein for determining a likelihood of a presence of one or more cardiovascular anomalies in a patient. The method may include determining a plurality of sets of image data corresponding to a plurality of style groups, each set of image data indicative of a portion of a sample patient's cardiovascular system and including a series of image frames, determining a plurality of representative sets of image data based on the plurality of sets of image data each including at least one representative image frame corresponding to one of the plurality of style groups, determining a first set of image data indicative of a first portion of the patient's cardiovascular system and including a first series of image frames, processing the first set of image data and each representative set of image data of the plurality of representative sets of image data using a style transfer generator to generate a set of styled image data for each representative set of image data, processing each set of styled set of image data for each representative set of image data using an image analyzer to determine the likelihood of a presence of one or more cardiovascular anomalies for each set of styled image data.

The method may further include, processing the plurality of sets of image data using a classification model to generate style data for each set of image data of the plurality of sets of image data. The style data may correspond to feature maps associated with each set of image data of the plurality of sets of image data. The method may further including processing the style data using a clustering model to determine a plurality of style groups corresponding to the plurality of sets of image data. The first set of image data may be generated by a first imaging system corresponding to a first imaging system type, the plurality of sets of image data may comprise a second set of image data generated by a second imaging system corresponding to a second imaging system type, and the first imaging system type may be different than the second imaging system type. The first imaging system may include a first imaging sensor corresponding to a first imaging sensor type and the second imaging system may include a second imaging sensor corresponding to a second imaging sensor type, the first imagining sensor type being a different from the second imaging sensor type. Determining a plurality of representative sets of image data may include using one or more of a Akaike Information Criterion (AIC) and a Bayesian Information Criterion (BIC).

The first set of image data may include one or more video clips having sequential image frames. The first set of image data may include a first image frame and a second image frame arranged immediately after the first image frame, and wherein processing the first set of image data and each representative set of image data of the plurality of representative sets of image data using the style transfer generator further comprises determining optical flow data based on the first image frame and the second image frame. The method may include determining at least one constrained region in the second image frame based on the optical flow data. The style transfer generator may be a convolutional neural network. The style transfer generator may be a recurrent neural network having an encoder-decoder portion and a multi-instance normalization portion, the recurrent neural network may be a spatiotemporal neural network.

A system is provided herein for determining a likelihood of a presence of one or more cardiovascular anomalies in a patient. The system may include memory designed to store computer-executable instructions and at least one computer processor designed to access memory and execute the computer-executable instructions to determine a plurality of sets of image data corresponding to a plurality of style groups, each set of image data indicative of a portion of a sample patient's cardiovascular system and including a series of image frames, determine a plurality of representative sets of image data based on the plurality of sets of image data each including at least one representative image frame corresponding to one of the plurality of style groups, determine a first set of image data indicative of a first portion of the patient's cardiovascular system and including a first series of image frames, process the first set of image data and each representative set of image data of the plurality of representative sets of image data using the style transfer generator to generate a set of styled image data corresponding to each representative set of image data, and process the styled set of image data using an image analyzer to determine the likelihood of a presence of one or more cardiovascular anomalies in the set of styled image data.

The computer processor may execute the computer-executable instructions to process the plurality of sets of image data using a classification model to generate style data for each set of image data of the plurality of sets of image data, the style data may corresponding to feature maps associated with each set of image data of the plurality of sets of image data, and process the style data using a clustering model to determine a plurality of style groups corresponding to the plurality of sets of image data. The first set of image data may be generated by a first imaging system that may correspond to a first imaging system type, the plurality of sets of image data may include a second set of image data generated by a second imaging system corresponding to a second imaging system type, and the first imaging system type may be different than the second imaging system type.

The first imaging system may include a first imaging sensor corresponding to a first imaging sensor type and the second imaging system may include a second imaging sensor corresponding to a second imaging sensor type, the first imagining sensor type may be different from the second imaging sensor type. Determining a plurality of representative sets of image data may include using one or more of a Akaike Information Criterion (AIC) and a Bayesian Information Criterion (BIC). The first set of image data may include one or more video clips having sequential image frames. The first set of image data may include a first image frame and a second image frame arranged immediately after the first image frame, and processing the first set of image data and each representative set of image data of the plurality of representative sets of image data using the style transfer generator may include determining optical flow data based on the first image frame and the second image frame. The computer processor may execute the computer-executable instructions to determine at least one constrained region in the second image frame based on the optical flow data. The style transfer generator may be a convolutional neural network. The style transfer generator may be a recurrent neural network having an encoder-decoder portion and a multi-instance normalization portion, the recurrent neural network may be a spatiotemporal neural network.

Yet another method is provided for determining a likelihood of a presence of one or more cardiovascular anomalies in a patient. The method may include determining a plurality of sets of image data corresponding to a plurality of style groups, determining representative image data corresponding to a representative style group, processing the plurality of sets of image data and the representative image data using a style transfer generator to generate a set of styled image data corresponding to the representative style group, training an image analyzer using the set of styled image data to determine the likelihood of a presence of one or more cardiovascular anomalies, determining a set of patient image data indicative of a portion of the patient's cardiovascular system, and processing the set of patient image data and the representative image data using a style transfer generator to generate a set of styled patient image data corresponding to the representative style group. The method may include processing the set of styled patient image data using the image analyzer to determine the likelihood of a presence of one or more cardiovascular anomalies present in the set of styled patient image data.

The set of patient image data may be generated by a first imaging system corresponding to a first imaging system type, the plurality of sets of image data may include a second set of image data generated by a second imaging system corresponding to a second imaging system type, and the first imaging system type may be different than the second imaging system type. The first imaging system may include a first imaging sensor corresponding to a first imaging sensor type and the second imaging system may include a second imaging sensor corresponding to a second imaging sensor type. The first imagining sensor type may be different from the second imaging sensor type. The set of patient image data may include one or more video clips having sequential image frames. The set of patient image data may include a first image frame and a second image frame arranged immediately after the first image frame, and wherein processing the set of patient image data using the style transfer generator further includes determining optical flow data based on the first image frame and the second image frame. The method may include determining at least one constrained region in the second image frame based on the optical flow data. The style transfer generator may be a convolutional neural network. The style transfer generator may be a recurrent neural network including an encoder-decoder portion and a multi-instance normalization portion, the recurrent neural network being a spatiotemporal neural network. The representative image data may include a representative image frame.

The foregoing summary is illustrative only and is not intended to be in any way limiting. In addition to the illustrative aspects, embodiments, and features described above, further aspects, embodiments, and features will become apparent by reference to the following drawings and the detailed description.

Figure 1:
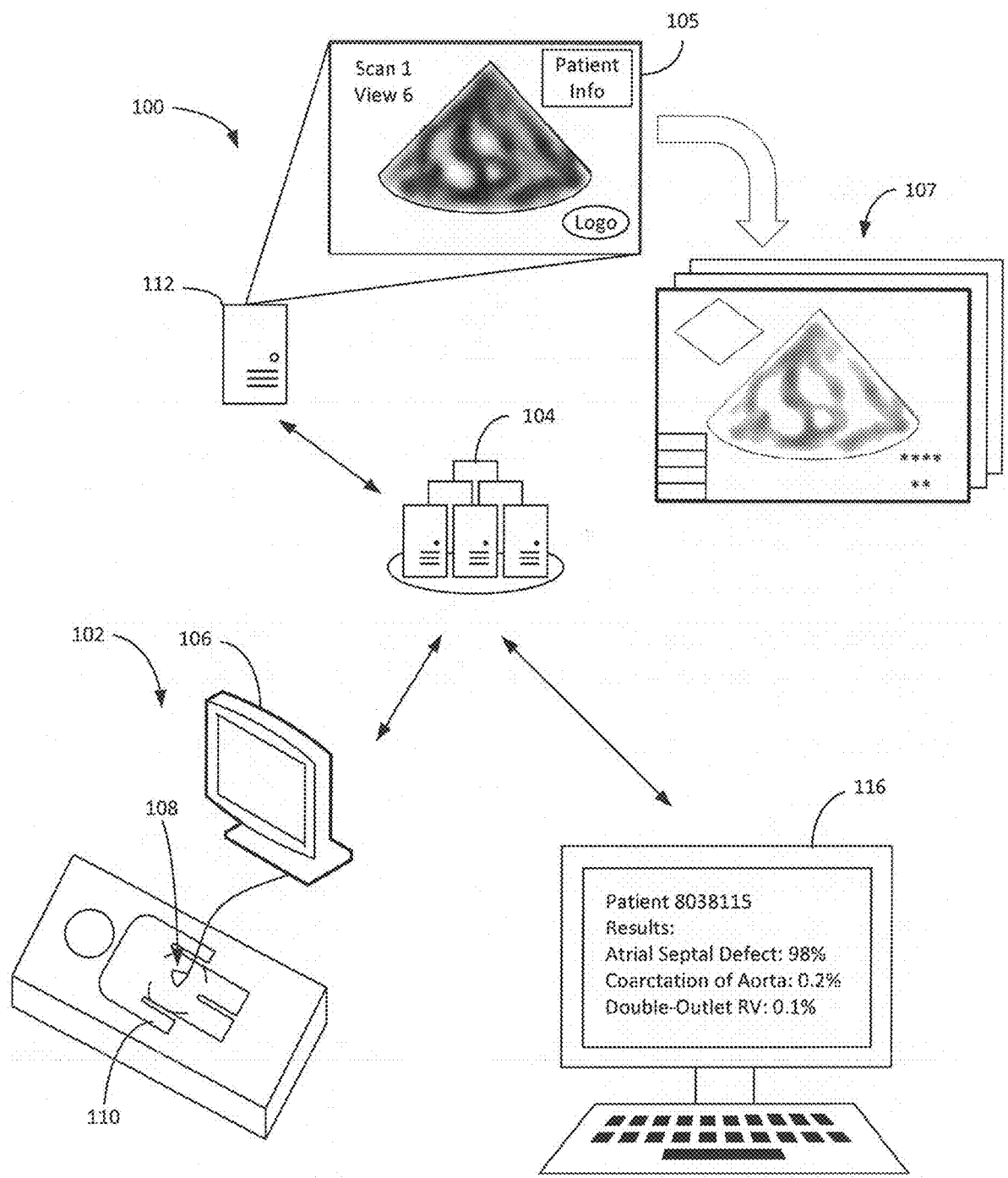
FIG. 1 illustrates an image processing system for determining styled input images and the presence of one or more cardiovascular anomalies, in accordance with some aspects of the present invention.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE INVENTION

The present invention is directed to an image processing system using artificial intelligence and machine learning to determine a likelihood of a presence of a cardiovascular anomaly, such as a congenital heart disease (CHD) and/or other cardiovascular related anomaly in a patient, such as a fetus during pregnancy. The image processing system may also optionally detect standard views, determine anatomy key-points, determine measurements, and/or perform segmentation. For example, medical imaging (e.g., still frames and/or video clips) may be generated using an imaging system such as an ultrasound system (e.g., an echocardiogram system) and may be processed by neural networks and/or models for determining a likelihood of a presence of one or more cardiovascular anomaly. The medical imaging may include a video clip and/or a consecutive series of still frame images.

The imaging processing system may overcome any biases in the system trained to detect a presence of the one or more cardiovascular anomaly, for example, by generating a set of styled image data for each set of input image data. Additionally, or alternatively, the images used for training may be styled to eliminate or reduce any bias. The set of styled input data may incorporate style data from representative style images from multiple different imaging systems. For example, a single input image frame may be styled using image data from several (e.g., four, eight, twenty, etc.) imaging systems, resulting in several input images, each corresponding to a representative style of a certain imaging system. The styled input images may be processed by an anomaly model (e.g., a classification neural network) for detecting cardiovascular anomalies in the set of styled input data.

The representative style images corresponding to each imagining system may be either determined using a classification and/or clustering model, may be derived from the image file itself (e.g., from metadata), or may be manually selected or determined. To accomplish style transfer for input video clips and/or series of consecutive images, various different approaches may be applied to maintain consistency between consecutive image frames. For example, the optical flow between frames may be determined and used to inform the style transfer such that certain regions of the consecutive frame may be constrained to maintain consistency between frames.

In yet another example, a style transfer model may be a neural network including an encoder-decoder portion and a multi-instance normalization portion. The neural network may be a spatiotemporal neural network. It is understood, however, that any other suitable approach for performing style transfer for input image frames and/or video clips may be used.

Referring now to FIG. 1, image processing system 100 is illustrated. Image processing system 100 may be designed to receive medical images, process medical images using artificial intelligence and machine learning, and determine a likelihood of a presence of one or more cardiovascular anomaly (e.g., CHD and/or other cardiovascular anomaly). For example, image processing system 100 may receive image data showing anatomy of a fetus and may process the image data to automatically determine a likelihood of a presence of one or more cardiovascular anomalies in the fetus. Additionally, image processing system 100 may optionally detect standard views, anatomy key-points, determine measurements, and/or perform segmentation.

Image processing system 100 may include one or more imaging system 102 that may each be in communication with a server 104. For example, imaging system 102 may be any well-known medical imaging system that generates medical image data (e.g., still frames and/or video clips including RGB pixel information) such as an ultrasound system, echocardiogram system, x-ray systems, computed tomography (CT) systems, magnetic resonance imaging (MRI) systems, positron-emission tomography (PET) systems, and the like.

As shown in FIG. 1, imaging system 102 may be an ultrasound imaging system including sensor 108 and imaging device 106. Sensor 108 may include a piezoelectric sensor device and/or transducer and/or may be any well-known medical imaging device. Imaging device 106 may be any well-known computing device including a processor and a display and may have a wired or wireless connection with sensor 108.

Sensor 108 may be used by a healthcare provider to obtain image data of the anatomy of a patient (e.g., patient 110). Sensor 108 may generate two or three-dimensional images corresponding to the orientation of sensor 108 with respect to patient 110. The image data generated by sensor 108 may be communicated to imaging device 106. Imaging device 106 may send the image data to remote server 104 via any well-known wired or wireless system (e.g., Wi-Fi, cellular network, Bluetooth, Bluetooth Low Energy (BLE), near field communication protocol, etc.).

Additionally, or alternatively, image data may be received and/or retrieved from one or more picture archiving and communication system (PACS). For example, the PACS system may use a Digital Imaging and Communications in Medicine (DICOM) format. Any results from the system may be shared with PACS.

Image data may be a set of image data, video clips, images, still frames, a series of consecutive image frames, or the like. For example, image data may include image 105, which may include a single frame of a two dimensional representation of a cross-section of a patient's cardiovascular anatomy (e.g., chambers of the heart). Image 105 may include certain information such as the patient's information, information about the number of scans, the video, the sensor device in use, the time, the data, the model of image device 106 and/or sensor 108, the company's and/or manufacturer's logo, the technician's name, a doctor's name, a name of a medical facility, and/or any other information commonly found on medical images.

Remote server 104 may be any computing device with one or more processors capable of performing operations described herein. In the example illustrated in FIG. 1, remote server 104 may be one or more server, desktop or laptop computer, or the like and/or may be located in a different location than imaging system 102. Remote server 104 may run one or more local applications to facilitate communication between imaging system 106, datastore 112, and/or analyst device 116.

Datastore 112 may be one or more drives having memory dedicated to storing digital information such as information unique to a certain patient, professional, facility and/or device. For example, datastore 112 may include, but is not limited to, volatile (e.g. random-access memory (RAM)), non-volatile (e.g. read-only memory (ROM)), flash memory, or any combination thereof. Datastore 112 may be incorporated into server 104 or may be separate and distinct from server 104. In one example, datastore 112 may be a picture archiving and communication system (PACS).

Remote server 104 may communicate with datastore 112 and/or analyst device 116 via any well-known wired or wireless system (e.g., Wi-Fi, cellular network, Bluetooth, Bluetooth Low Energy (BLE), near field communication protocol, etc.). Datastore 112 may receive and store image data (e.g., image data 118) received from remote server 104.

For example, imaging system 102 may generate image data (e.g., ultrasound image data) and may send such image data to remote server 104, which may send the image data to datastore 112 for storage. It is understood that datastore 112 may be optional and/or more than one imaging system 102, remote server 104, datastore 112 and/or analyst device 116 may be used.

Analyst device 116 may be any computing device having a processor and a display and capable of communicating with at least remote server 104 and performing operations described herein. Analyst device 116 may be any well-known computing device such as a desktop, laptop, smartphone, tablet, wearable, or the like. Analyst device 116 may run one or more local applications to facilitate communication between analyst device 116 and remote server 104 and/or any other computing devices or servers described herein.

Remote server 104 may determine and/or receive representative images corresponding to unique styles for various types of imaging systems. While FIG. 1 illustrates server 104 in communication with imaging system 106, server 104 may be in communication with multiple different imaging systems that may include different types of imaging systems (e.g., imaging systems with different sensors, different hardware, different software, imaging systems made by different companies and/or manufacturers, different model numbers, etc.). Alternatively, server 104 may receive images from datastore 112.

Remote server 104 may receive sets of input image data (e.g., video clips and/or image frames) from imaging system 106 and/or datastore 112 and may extend the input image data into multiple types of input image data, incorporating the styles of the various different types of imaging systems into the input image data (e.g., styled images 107). Style may alternatively, or additionally, refer to a look or feel of the images generated by a probe that may be a result of a patient's anatomy. For example, style could include a patient's BMI and/or age which may result in a certain look in the medical imaging. Remote server 104 may process the styled input image data using one or more trained models such as neural networks (e.g., convolutional neural networks (CNNs)) trained to detect one or more cardiovascular anomalies. For example, a likelihood of a presence of one or more cardiovascular anomalies may be determined and may optionally be automatically processed by remote server 104 to determine a presence of one or more cardiovascular anomaly. In one example, remote server 104 and/or datastore 112 may facilitate storage, processing, and/or analysis in the cloud.

Remote server 104 may share information regarding a likelihood of a presence of one or more cardiovascular anomalies with one or more computing device (e.g., user device, analyst device, medical device, practitioner device, etc.). Remote server 104 may cause analyst device 116 to display information about the likelihood of a presence of one or more cardiovascular anomalies. For example, analyst device may display a patient ID number and a likelihood percentage for one or more CHDs and/or other cardiovascular anomalies.

Figure 2:
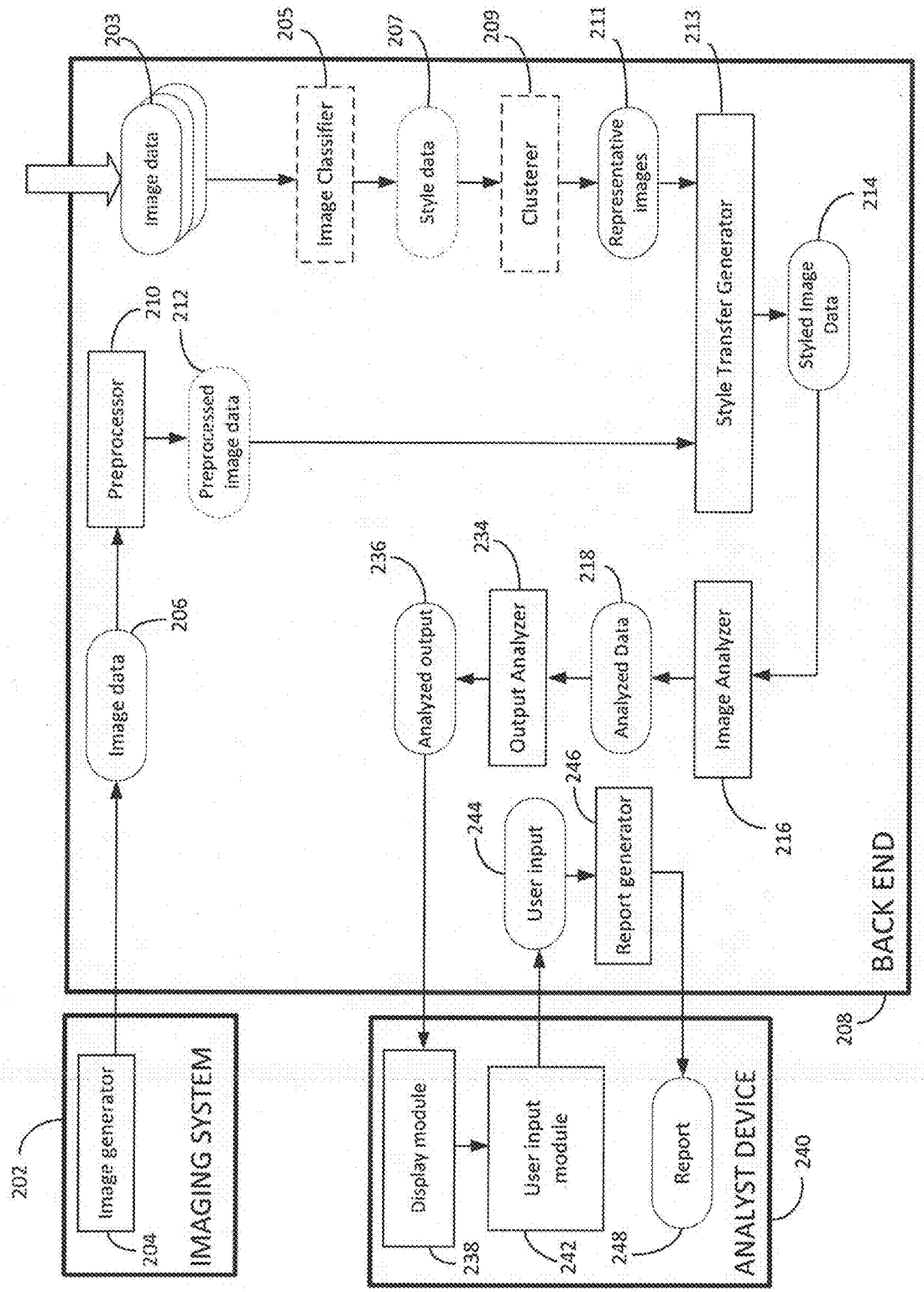
FIG. 2 illustrates a schematic view of data flow between an imaging system, analyst device, and back end of an image processing system.

Referring now to FIG. 2, a schematic view of the data flow between an imaging system, analyst device, and back end of the image processing system is depicted. As shown in FIG. 2, imaging system 202, which may be the same as or similar to imaging system 102 of FIG. 1, may include image generator 204 which may generate image data 206. Image data 206 may include video clips and/or still frames, which may include RGB and/or grey scale pixel information.

Alternatively, or additionally, image data 206 may include Doppler image data. Imaging system 202 may be designed to generate grey scale image data and/or Doppler image data. For example, image data 206 may include two-dimensional representations of ultrasound scans of the patient's (e.g., a fetus' anatomy). Additionally, or alternatively, image data 206 may include Doppler image information (e.g., color Doppler, power Doppler, spectral Doppler, Duplex Doppler, and the like). It is understood that various types of image data 206 may be simultaneously processed by imaging system 202. In one example, the Doppler image data may be generated at the same time as ultrasound image data.

Imaging system 202 may send image data 206, which may be input image data (e.g., set of input image data) to backend 208, which may be the same as or similar to server 104 of FIG. 1. Image data 206 may optionally be processed by preprocessor 210. Preprocessor 210 may remove noise, reduce file size, focus, crop, resize and/or otherwise remove unnecessary areas of image data 206 to generate preprocessed image data 212. Preprocessor may additionally, or alternatively, generate a consecutive series of still frame images from video clips or otherwise may segment video clips.

Image data 206 may be applied to style transfer generator 213, which may be trained using representative images 211. Applying the image data to the style transfer generator is understood throughout to mean either applying the image data to the style transfer generator or applying to the style transfer generator to the image data such that the image data is processed by, input into, and/or analyzed by the style transfer generator. Representative images 211 may be manually selected from image data with known styles. For example, style may be known as it may correspond to certain recording echographs and/or probes (e.g., of a certain model or manufacturer) and/or the style may be determined from metadata or other information in the image file. Alternatively, image classifier 205 and clusterer 209 may be used to determine representative images 212 from image data 203.

Image data 203, which may be multiple sets of image data (e.g., video clips and/or image frames) from various different types of imaging devices, systems, models, units, etc., may be received by backend 208. For example, image data 203 may include video clips representative of medical images of cardiovascular portions of various patients. It is understood that image data 203 may be a large volume of image data (e.g., hundreds, thousands, or more of video clips) and may be received by backend 208 at different times. In one example, image data 203 may optionally be preprocessed by a processor similar to preprocessor 210.

Where style is not known and/or representative images 211 are not manually selected, image data 203 may be processed by image classifier 205. Image classifier 205 may be a neural network such as a classification neural network that may be trained for image processing, detection, and/or recognition using large sets of images. For example, images from daily life (e.g., cars, bikes, apples, etc.) may be used to train the classifier generally for image recognition. Additionally, or alternatively, the classifier may be trained or fine-tuned using specific datasets corresponding to cardiovascular anatomy including with and/or without CHD and/or other cardiovascular anomalies to ultimately recognize cardiovascular anomalies.

Image classifier 205 may be used to determine style data 207, which may be based on low-level feature maps (e.g., in the early layers of the neural network) of classifier 205. For each image (e.g., still frame) of image data 203 processed by classifier 205, Gram matrices for feature maps corresponding to that image may be computed. For example, each Gram matrix may be a representation of the feature maps of an image at a certain layer (e.g., using a correlation operation). In one example, the Gram matrix may contain dot products of the feature maps.

The values of the Gram matrices may be concatenated into vectors (e.g., a single style vector). Style data may include the low-level feature maps or representations thereof, corresponding Gram matrices, and/or one or more vectors corresponding to the Gram matrices. Clusterer 209 may process the vectors representing Gram matrices and may determine a position (e.g., data point) within a multi-dimensional space based on the vector. Clusterer may be any suitable cluster model trained to perform clustering (e.g., clustering of the Gram matrices. In one example, clustering may be performed using a Gaussian Mixture Model (GMM) method.

Once clustering has been performed on the vectors representative of the Gram matrices, groups of imaging system styles may be identified in the multi-dimensional space based on a proximity representations of such input vectors. For example, data points in relatively close proximity to one another may be determined to be in the same cluster, referred to herein as style group. Each image or image set corresponding to data points in the same cluster will thus be determined to have a similar style. Style may be the arrangement or presentation or images and/or data in the image (e.g., border style, text placement, size, or font, general image style, certain colors, or the like).

For each style group, a representative set of images or image frames may be determined. For example, the image corresponding to the data point in the center-most position of the style group in the multi-dimensional space may be determined. In one example, a representative data-point for a given style group in the multi-dimensional space may be determined using Akaike Information Criterion (AIC) and/or Bayesian Information Criterion (BIC). However, it is understood that any other suitable approach may be used for determining a data-point in the multi-dimensional space that best represents a given style group.

The image data used to determine the Gram matrix and vector input to the clusterer, ultimately resulting in the representative style data point, may be determined, referred to as representative image 211. Representative image 211 may thus contain style data 207 that best represents a style group which may correspond to a given type of imaging system. The representative image for each style group in the multi-dimensional space may be determined in the same manner. Representative images 211 may be a set of image frames, a single image frame, and/or a video clip.

Whether representative images 211 were manually selected or determined using image classifier 205 and clusterer 209, both input image data 206 and representative images 211 may be input and processed by style transfer generator 213 to extend input image data 206 into multiple image frames, each incorporating a representative style for each style group identified by clusterer 209. For example, for each representative image 211, a styled input may be generated by style transfer generator 213. Alternatively, instead of using image classifier 205 and cluster 209 to determine representative images 211, representative images 211 may be manually determined and provided to back end 208.

Style transfer generator 213 may be a model (e.g., one or more neural networks) trained to combine the content of image data 206 with the style of one image of representative image 212, resulting in an image frame having the content of image data 206 and the style of image data 203. Style transfer generator 213 may be trained to transfer style for a given image frame and/or may transfer style for a given video clip. For example, style transfer generator 213 may be trained with images for which a style corresponding to such images is known. Optionally, other information corresponding to the training set of images may also be known such as a manufacturer of the imaging system, a model number, a probe type or style, a patient condition and/or other biometric information, and/or the like may be known. Based on this information the model may be trained to map a given input image to any known style. This type of training may be supervised training.

In the example where the style transfer generator 213 transfers style for a given image frame, style transfer generator 213 may use the technique set forth in "A Neural Algorithm of Artistic Style," by L. Gatys, et. al, arXiv: 1508.06576v2, Sep. 2, 2015, incorporated herein by reference in its entirety. Specifically, the feature map for a representative image may be determined using a convolutional neural network. For example, lower levels of the convolutional neural network (CNN) may be used to determine, approximate, represent, and/or extract the style information. Additionally, the input image (e.g., image data 206) may be processed by the CNN to determine content information. For example, in higher layers of the CNN, high level content information may be determined, approximate, represent, and/or extracted.

The style information from the representative image (e.g., representative image 211) and the content information from the input image (e.g., from image data 206) may be synthesized by finding an image that simultaneously matches the content information of the input image and the style information of the representative image.

Rather than performing style transformation for a single image frame in isolation, it may be desirable to perform style transformation for a video clip or multiple image frames in series. For example, style transformation may be performed using the style transfer generator 213 and the approach outlined in "Artistic style transfer for videos and spherical images" by Ruder, et. al, arXiv:1708.04538v3, Aug. 5, 2018, incorporated herein by reference in its entirety. Specifically, style transformation may be performed on a video clip (e.g. a series of consecutive image frames) in a manner that styles each image frame based in part by the image frame that came before it. For example, deviations between two consecutive image frames may be determined by determining an optical flow for the image frames. With known deviations, a multi-pass algorithm may be used to process the video clip in alternating temporal directions using both forwards and backwards flow. To maintain consistency in the video clip, a constrained region may be determined based on the optical flow for each image frame and each subsequent image frame may be styled based on, at least in part, the previously styled image frame in the series, taking the previously styled image frame as input, warped according to the optical flow.

In another example, style transformation for a video clip may include using the style transfer generator 213 and the approach outlined in "Real-Time Neural Style Transfer for Videos," H. Huang, et. al, Conference: 2017 IEEE Conference on Computer Vision and Pattern Recognition (CVPR), Jul. 1, 2017, incorporated herein by reference in its entirety. For example, the style transfer model may be a feed-forward convolutional neural network including a styling network and a loss network. The stylizing network may process input image frames and output styled image frames. The loss network may include a classification network to determine, approximate, represent, and/or extract features of the styled image frames and output loss data indicative of spatial loss in each of the styled stylized image frames. In addition to spatial loss, which leads to style transfer for each frame, the style transfer model may further incorporate temporal loss to enforce the temporal consistency between adjacent frames. To determine temporal loss, two consecutive frames are fed into the network, simultaneously. The temporal loss is defined as the mean square error between the styled output at time t and the warped version of the styled output at time t−1.

In yet another example, style transformation for a video clip using style transfer generator 213 based on the approach outlined in "Fast Video Multi-Style Transfer" by W. Gao, Conference: 2020 IEEE Conference Winter Conference on Applications of Computer Vision (WAVC), Mar. 1-5, 2020, incorporated herein by reference in its entirety. For example, style transfer generator 213 may include multiple modules such as an encoder-decoder, a multi-instance normalization block, and a convolutional long short term memory (ConvLSTM). To avoid retraining the network for each different style, the network may learn multiple styles using the instance normalization layer with multiple sets of parameters. For example, each style may be associated with a certain pair of parameters. Each parameter pair can be regarded as the embedding of a specific style in the instance normalization layer. The ConvLSTM may be two ConvLSTM modules that may be inserted into the encoder-decoder network. Using a recurrent network, for example, may combine all previous frame information and current frame information to infer the output. Specifically, the ConvLSTM may compress the whole previous input sequence into a hidden state tensor and may forecast the current state based on the hidden state.

Using style transfer generator 213, which may use any of the style transfer approach described herein and/or any other suitable style transfer approach, styled image data 214 may be generated. Style image data may include multiple image frames, each corresponding to image data 206 but with a different style. For example, an image frame for each style identified (e.g., by clustered 209 or manually) may be generated for each image frame of image data 206. For example, if eight styles are determined, then eight distinct image frames may be generated by style transfer generator 213, each with a different style but with the content of image data 206.

In another example, image analyzer 216 may be trained using image data that was styled (e.g., using style transfer generator 213) according a certain style (e.g., a standard style). Image data 206 may then be analyzed by image analyzer 216. Alternatively, image data 206 may also be applied to style transfer generator 213 to be styled with the same style (e.g., the standard) that the training data was styled with. In this example, style transfer generator 213 may only output styled images for each input image (e.g., each image of image data 206) based on the same style type (e.g., the standard style).

Each image frame in styled image data 214 may be processed by image analyzer 216. Image analyzer 216 may be one or more neural networks trained to process image data (e.g., image frames and/or video clips), such as medical image data, to detect cardiovascular anomalies (e.g., CHD) and optionally determine or detect standard views, anatomy key-points (e.g., identifying extremities of the valves), measurements (e.g., measure the size of the heart and/or area or volume of the heart), and/or perform segmentation (e.g., identify the contour of the heart). For example, image analyzer 216 may process styled image data 214 and may detect one or more cardiovascular anomaly in each image frame.

In one example, image analyzer 216 may be a spatiotemporal CNN trained to determine cardiovascular anomalies. For example, image analyzer 216 may include a spatial stream and a temporal stream that may be fused together. Styled image data may be applied to a spatial model, which may be a spatial CNN such as a spatial CNN trained for image processing, to generate a spatial output. Additionally, optical flow data may be generated based on styled image data 214, which may permit the networks to better consider the movement of the image data over time.

The optical flow data may be applied to a temporal model, which may be a temporal CNN such as a temporal CNN trained for image processing and/or trained for processing optical flow data to generate a temporal output. The spatial output and temporal output may both be input into a fuser to generate a spatiotemporal output. For example, the fuser may combine architecture of the spatial model and the temporal model at several levels.

In another example, as explained above, image analyzer 216 may be trained using image data that has been applied to style transfer generator 213, resulting in a training data set having all the same style (e.g., a standard style). As a result, image analyzer 216 may avoid or lessen any bias for a certain style because all the input images used for training purposes may now have the same style. In this example, image data 206, prior to being input into image analyzer 216, may optionally be processed by style transfer 213 to transfer the same style used for the training data to image data 206.

Image analyzer 216 may output analyzed data 218, which may be indicative of a likelihood of a presence of one or more anomalies in the styled image data, and optionally a presence of a standard view, anatomy key-point, measurement information, and/or segmentation information. For example, a value between 0 and 1 may be generated for each type of potential anomaly and may be indicative of the presence of that particular anomaly. Alternatively, any other suitable image processing model (e.g., a classification model) may be used for processing styled image data 214 and detecting a likelihood of a presence of one or more cardiovascular anomalies in styled image data 214.

Analyzed data 218 may be processed by output analyzer 234 which may generate analyzed output 236 which may indicate a presence of one or more cardiovascular anomalies in styled image data 214. For example, output analyzer 234 may calculate weighted averages based on analyzed data 218 and/or may filter certain portions of analyzed data 218. In one example, analyzed output 236 may indicate the risk of a likelihood of a presence of one or more morphological abnormalities or defects and/or may indicate the presence of one or more pathologies. For example, analyzed output 236 may indicate the presence of atrial septal defect, atrioventricular septal defect, coarctation of the aorta, double-outlet right ventricle, d-transposition of the great arteries, Ebstein anomaly, hypoplastic left heart syndrome, interrupted aortic arch, ventricular disproportion (e.g., the left or right ventricle larger than the other), abnormal heart size, ventricular septal defect, abnormal atrioventricular junction, increased or abnormal area behind the left atrium, abnormal left ventricle and/or aorta junction, abnormal right ventricle and/or pulmonary artery junction, great arterial size discrepancy (e.g., aorta larger or smaller than the pulmonary artery), right aortic arch abnormality, abnormal size of pulmonary artery, transverse aortic arch and/or superior vena cava, a visible additional vessel, and/or any other morphological abnormality, defect and/or pathology. It is understood that, in one example, analyzed output 236 may be indicative of one or more CHD or may be indicative of features associated with one or more CHD.

Back end 208 may communicate analyzed output 236 and/or information based on analyzed data 218 to analyst device 240, which may be the same as or similar to analyst device 116. Analyst device 240 may be different than or the same as the device in imaging system 202. Display module 238 may generate a user interface on analyst device 240 to generate and display a representation of analyzed output 236 and/or analyzed data 218. For example, the display may show a representation of the image data (e.g., ultrasound image) with an overlay indicating the location of the detected risk or likelihood of CHDs and/or other cardiovascular anomalies. In one example, the overlay could be a box or any other visual indicator (e.g., arrow).

User input module 242 may receive user input 244 and may communicate user input 244 to back end 208. User input 244 may be instructions from a user to generate a report or other information such as instructions that the results generated by one or more of image classifier 205, clusterer 209, style transfer generator 213, image analyzer 216, and/or output analyzer 234, are not accurate. For example, where user input 244 indicates an inaccuracy, user input 244 may be used to further train one or more of the foregoing models and/or networks.

Where user input 244 indicates a request for a report, user input 244 may be communicated to report generator 246, which may generate a report. For example, the report may include some or all of analyzed output 236, analyzed data 218 and/or analysis, graphs, plots, tables regarding the same. Report 248 may then be communicated to analyst device 240 for display (e.g., by display module 238) of report 248, which may also be printed out by analyst device 240.

Figure 3:
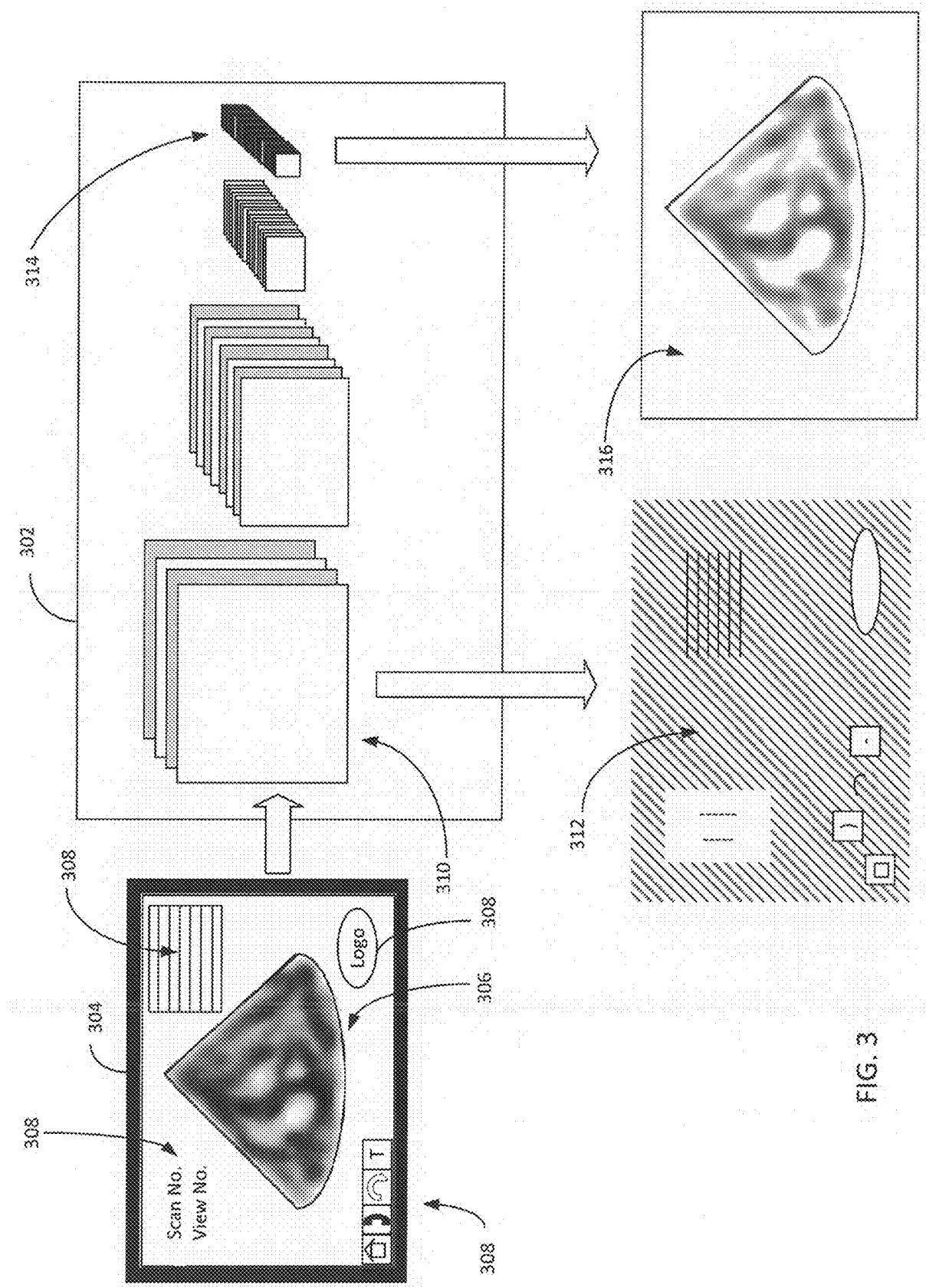
FIG. 3 illustrates a schematic view of a classification model for determining content data and style data.

Referring now to FIG. 3, a classification model for determining content data and style data is depicted. For example, the model 302 may be the same as or similar to image classifier 205 of FIG. 2. As shown in FIG. 3, image frame 304 may be input into model 302. Image frame 304 may be similar to image 105 of FIG. 1 and may include a single frame of a two dimensional representation of a cross-section of a patient's cardiovascular anatomy (e.g., chambers of the heart).

Image frame 304 may include content data 306, which may show the representation of the patient's anatomy. Additionally, image frame 304 may include style data 308 including certain style information such as the patient's information, information about the number of scans, the video, the sensor device in use, the time, the data, the model of image device 106 and/or sensor 108, the company's and/or manufacture's logo, the technician's name, a doctor's name, a name of a medical facility, and/or any other information commonly found on medical images. Style data 308 may further include the look and/or feel of the image such as colors, spatial arrangement, text style, text font, borders, icons for navigation and the like. Alternatively, or additionally, information about the imaging device (e.g., model and/or make) and/or other style information may be determined from image file information such as metadata and/or in other information in a Digital Imaging and Communications in Medicine (DICOM) files, for example.

Feature maps from low levels 310 of a model 302 may be used to determine, approximate, represent, and/or extract style data 312 which may capture the texture and other style information of the image. Style data 312 may be representative of style data 308, but without content data 306. For example, style data 312 may include nuances such as contrast, tint, colors, clarity, edges, and the like. Additionally, in higher layers 314 of model 302, content data 316 may be determined. Content data 316 may be representative of content data 306 and may include a representation of the patient's anatomy. In this manner, one or more neural networks may map one image to a similar image (e.g., with the same content) but with a certain style.

Figure 4:
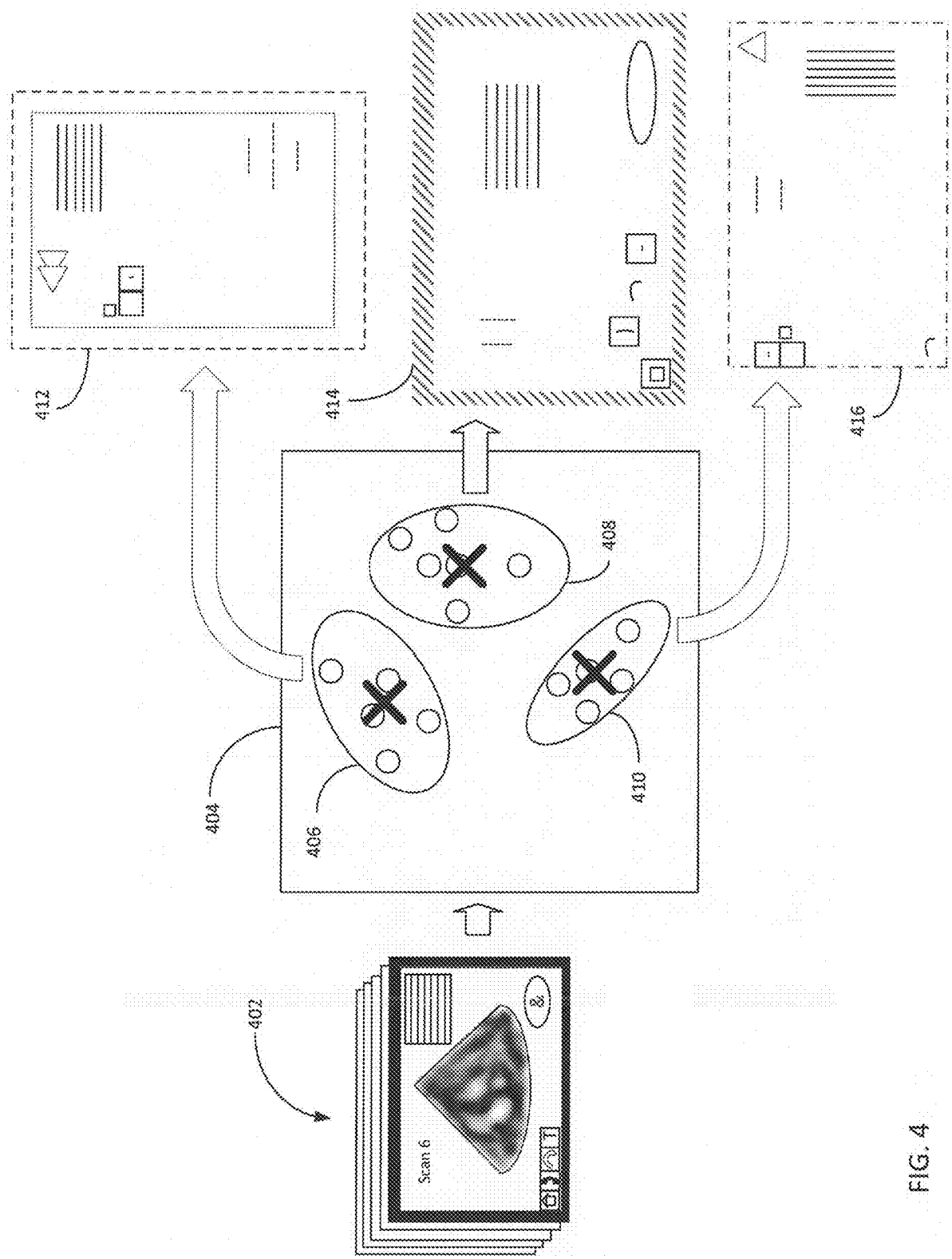
FIG. 4 illustrates a schematic view of a clustering model for determining style groups.

Referring now to FIG. 4, a clustering model for forming style groups and style data corresponding to each style group is illustrated. As shown in FIG. 4, set of input data 402, which may be the same or similar to image data 206 (e.g., input data and/or set of input data), may be processed by an image classier to determine style data. The style data may be represented by vectors which may then be processed by a clusterer which may output spatial information representing the style data in multi-dimensional space 404. While a two-dimensional plot is illustrated in FIG. 4, it is understood more than two dimensions may be generated.

Multi-dimensional space 404 may be used to indicate multiple distinct groups of style groups, which may be groups or clusters of data points representative of images having style data that are in close proximity in multi-dimensional space 404. For example, style group 406, style group 408, and style group 410 may be determined from multi-dimensional space 404. Each data point in a given style group may represent style data having similar style. For example, style group 406 may correspond to image data generated using the same ultrasound software resulting in a similarly arranged image.

As shown in FIG. 4, style data 412, which may correspond to style group 406, may be representative of an image with a light border, text and navigation icons on the top and arranged in portrait orientation. Style data 414, which may correspond to style group 408, may be presentative of an image with a dark border, text in the top right, a logo in the bottom right, and navigation icons in the bottom left. Style data 416, which may correspond to style group 410, may be representative of an image with no border, text data on the right as well as a logo or other image, and some navigation icons on the left. While each data point in each style group may not correspond to exactly the same type of style data, the close proximity in multi-direction space 404 indicates at least some similarities in the style arrangement or selection.

Figure 5:
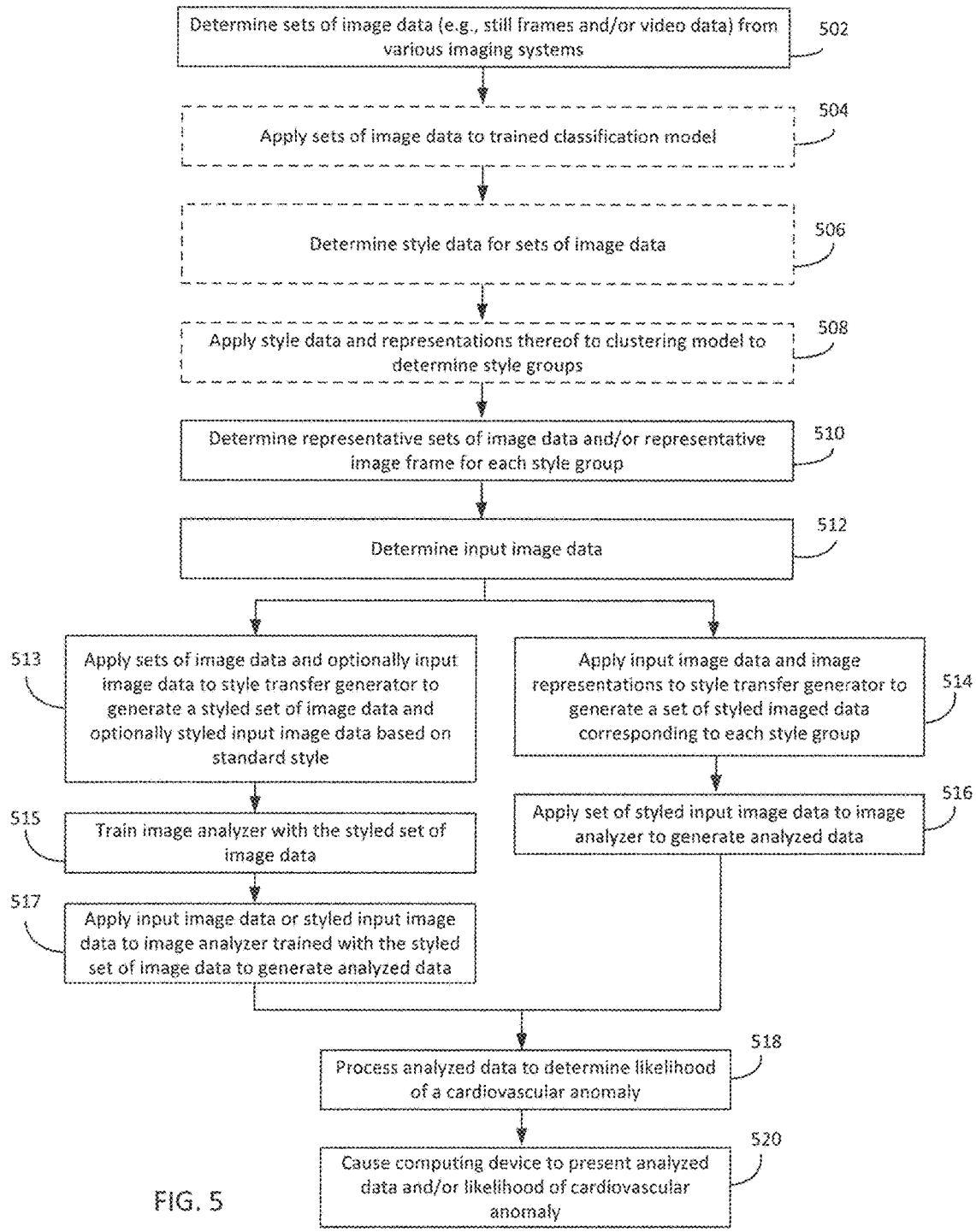
FIG. 5 illustrates process flows for determining representative style images, styled input images based on the representative style images, and determining a likelihood of a presence of a cardiovascular anomaly.

Referring now to FIG. 5, a process flow is depicted for indicating a likelihood of CHD and/or other cardiovascular anomaly agnostic of a type of imaging system (e.g., ultrasound), transducer and/or sensor, and/or other style inputs. Some or all of the blocks of the process flows in this disclosure may be performed in a distributed manner across any number of devices (e.g., a server such as server 104 of FIG. 1, computing devices, imaging or sensor devices, or the like). Some or all of the operations of the process flow may be optional and may be performed in a different order.

At block 502, computer-executable instructions stored on a memory of a device, such as a server, may be executed to determine sets of image data (e.g., still frames and/or video data) from one or more imaging system. For example, the sets of image data may be generated by different imaging systems made from different companies, manufacturers, and/or having different sensors and/or hardware. At optional block 504, computer-executable instructions stored on a memory of a device, such as a server, may be executed to apply the sets of image data to a trained classification model (e.g., image classifier 205 of FIG. 2).

At optional block 506, computer-executable instructions stored on a memory of a device, such as a server, may be executed to determine style data from the sets of image data. For example, low-level feature maps from the trained classification model may be used to determine style data for the sets of image data. At optional block 508, computer-executable instructions stored on a memory of a device, such as a server, may be executed to apply the style data and/or representations of the style data to a clustering model (e.g., clusterer 209 of FIG. 2) to determined style groups. For example, Gram matrices corresponding to low layers of the classification model may be determined and vectors representative of such Gram matrices may be input into the clustering model.

At block 510, computer-executable instructions stored on a memory of a device, such as a server, may be executed to determine representative sets of image data and/or representative image frames for each style group. For example, a representative data point for a given style group in the multi-dimensional space may be determined using any suitable approach for determining a data point in the multi-dimensional space that best represents a given style group. Alternatively, a representative image frame for each style may be manually selected.

At block 512, computer-executable instructions stored on a memory of a device, such as a server, may be executed to determine input image data (e.g., sets of input image data, image frames, and/or a video clip). Input image data may be the same as or similar to image data 206 of FIG. 2. At block 514, computer-executable instructions stored on a memory of a device, such as a server, may be executed to process the input image data using a style transfer generator (e.g., style transfer generator 213). The representative image frames from block 510 may also be input into the style transfer generator. The style transfer generator may output a set of styled imaged data (e.g., styled image data 214 of FIG. 2) for each style determined (e.g., for each style group). For example, if five styles are determined, the style transfer generator may generate five distinct styled images for each input image data, each styled imaged corresponding to one of the five styles.

At block 516, computer-executable instructions stored on a memory of a device, such as a server, may be executed to apply the set of styled image data to an image analyzer (e.g., image analyzer 216 of FIG. 2) to generate analyzed data (e.g., analyzed data 218 of FIG. 2). It is understood that the image analyzer may optionally determine or detect standard views, anatomy key-points, measurements, and/or perform segmentation. In the example where multiple different styled images are output by the style transfer generator for a given input image, the analyzed data may be aggregated resulting in aggregated analyzed data. For example, where the analyzed data is a vector or matrix, each vector or matrix may be added or otherwise combined resulting in a single vector or matrix.

As an alternative to blocks 514-516, the image analyzer may be trained using styled training data. In this example, at block 513, computer-executable instructions stored on a memory of a device, such as a server, may be executed to apply the set of image data (e.g., the training data) and optionally the input image data to the style transfer generator to generate one or more styled sets of image data and/or styled input image data based multiple different style types or alternatively, based on a single standard style. At block 515, computer-executable instructions stored on a memory of a device, such as a server, may be executed to train the image analyzer using the styled set or sets of image data. In one example, the training data may be styled with multiple different types of styles such that for each image frame of training data, multiple styled image frames may be generated, depending on the number of styles. Alternatively, the training data may be styled with only one style, which may be the standard style. At block 517, the input image data or the styled input image data may be applied to and/or processed by the image analyzer to generate analyzed data.

After either block 516 or 517, block 518 may be initiated, at which computer-executable instructions stored on a memory of a device, such as a server, may be executed to process the analyzed data and/or aggregated analyzed data to determine likelihood of a cardiovascular anomaly. For example, analyzed data and/or aggregated analyzed data may be a number between 0 and 1 and the analyzed data and/or aggregated analyzed data may be processed to determine if the anomaly satisfies a certain threshold value (e.g., 0.7), in which case it may be determined that a cardiovascular anomaly is likely present. At block 520, computer-executable instructions stored on a memory of a device, such as a server, may be executed to cause a computing device (e.g., an analyst device or any other device) to present the analyzed data and/or likelihood of cardiovascular anomaly on a computing device (e.g., analyst device).

Figure 6:
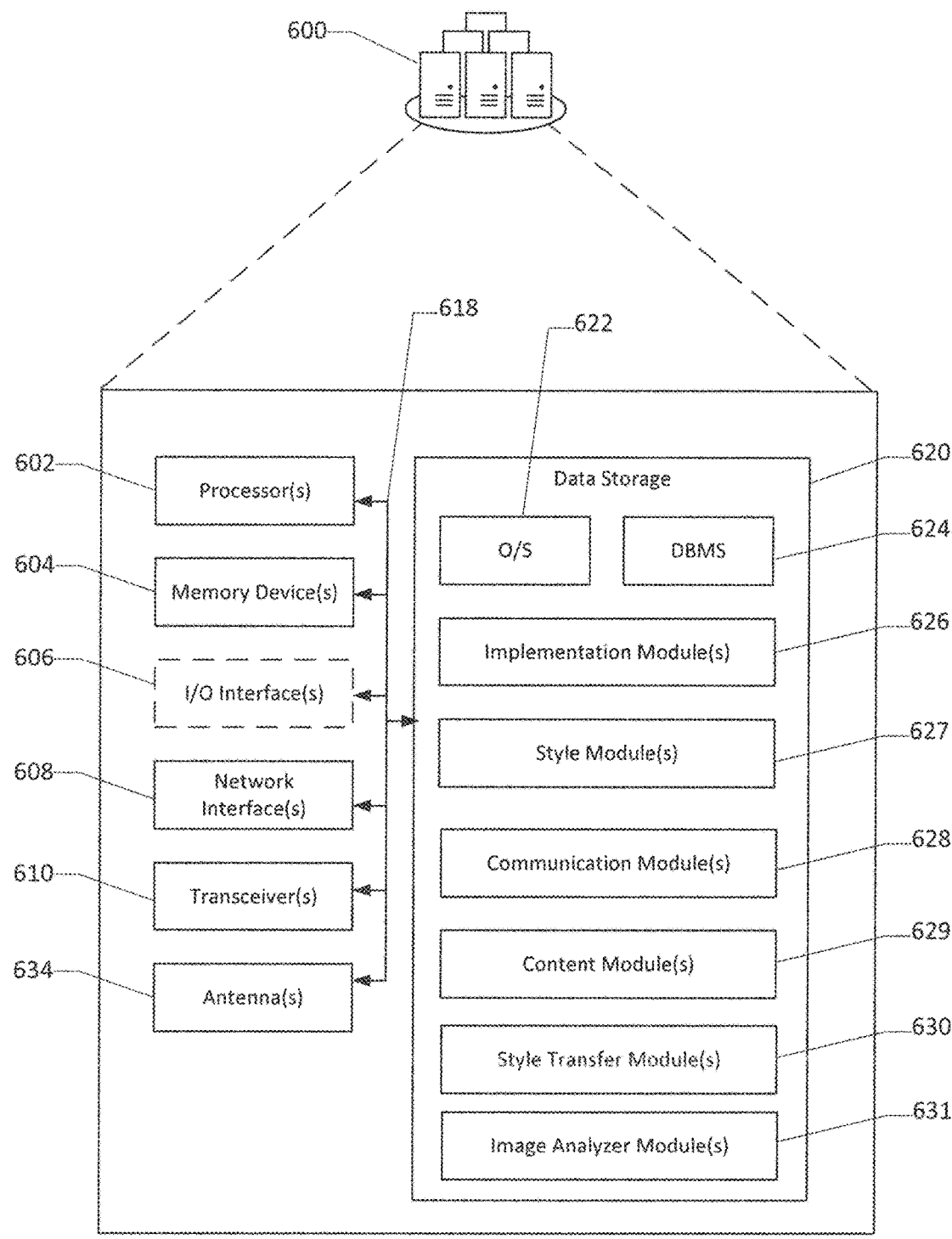
FIG. 6 is a schematic block diagram of a computing device.

Referring now to FIG. 6, a schematic block diagram of server 600 is illustrated. Server 600 may be the same or similar to server 104 of FIG. 1 or otherwise one or more of the servers of FIGS. 1-5B. It is understood that an imaging systems, analyst device and/or datastore may additionally or alternatively include one or more of the components illustrated in FIG. 6 and server 600 may alone or together with any of the foregoing perform one or more of the operations of server 600 described herein.

Server 600 may be designed to communicate with one or more servers, imaging systems, analyst devices, data stores, other systems, or the like. Server 600 may be designed to communicate via one or more networks. Such network(s) may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks.

In an illustrative configuration, server 600 may include one or more processors 602, one or more memory devices 604 (also referred to herein as memory 604), one or more input/output (I/O) interface(s) 606, one or more network interface(s) 608, one or more transceiver(s) 610, one or more antenna(s) 634, and data storage 620. The server 600 may further include one or more bus(es) 618 that functionally couple various components of the server 600.

The bus(es) 618 may include at least one of a system bus, a memory bus, an address bus, or a message bus, and may permit exchange of information (e.g., data (including computer-executable code), signaling, etc.) between various components of the server 600. The bus(es) 618 may include, without limitation, a memory bus or a memory controller, a peripheral bus, an accelerated graphics port, and so forth. The bus(es) 618 may be associated with any suitable bus architecture.

The memory 604 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In various implementations, the memory 604 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth.

The data storage 620 may include removable storage and/or non-removable storage including, but not limited to, magnetic storage, optical disk storage, and/or tape storage. The data storage 620 may provide non-volatile storage of computer-executable instructions and other data. The memory 604 and the data storage 620, removable and/or non-removable, are examples of computer-readable storage media (CRSM) as that term is used herein. The data storage 620 may store computer-executable code, instructions, or the like that may be loadable into the memory 604 and executable by the processor(s) 602 to cause the processor(s) 602 to perform or initiate various operations. The data storage 620 may additionally store data that may be copied to memory 604 for use by the processor(s) 602 during the execution of the computer-executable instructions. Moreover, output data generated as a result of execution of the computer-executable instructions by the processor(s) 602 may be stored initially in memory 604, and may ultimately be copied to data storage 620 for non-volatile storage.

The data storage 620 may store one or more operating systems (O/S) 622; one or more optional database management systems (DBMS) 624; and one or more program module(s), applications, engines, computer-executable code, scripts, or the like such as, for example, one or more implementation modules 626, style module 627, communication module 628, content module 629, style transfer module 630, and/or image analyzer module 631. Some or all of these modules may be sub-modules. Any of the components depicted as being stored in data storage 620 may include any combination of software, firmware, and/or hardware. The software and/or firmware may include computer-executable code, instructions, or the like that may be loaded into the memory 604 for execution by one or more of the processor(s) 602. Any of the components depicted as being stored in data storage 620 may support functionality described in reference to correspondingly named components earlier in this disclosure.

Referring now to other illustrative components depicted as being stored in the data storage 620, the O/S 622 may be loaded from the data storage 620 into the memory 604 and may provide an interface between other application software executing on the server 600 and hardware resources of the server 600. More specifically, the O/S 622 may include a set of computer-executable instructions for managing hardware resources of the server 600 and for providing common services to other application programs (e.g., managing memory allocation among various application programs). In certain example embodiments, the O/S 622 may control execution of the other program module(s) for content rendering. The O/S 622 may include any operating system now known or which may be developed in the future including, but not limited to, any server operating system, any mainframe operating system, or any other proprietary or nonproprietary operating system.

The optional DBMS 624 may be loaded into the memory 604 and may support functionality for accessing, retrieving, storing, and/or manipulating data stored in the memory 604 and/or data stored in the data storage 620. The DBMS 624 may use any of a variety of database models (e.g., relational model, object model, etc.) and may support any of a variety of query languages. The DBMS 624 may access data represented in one or more data schemas and stored in any suitable data repository including, but not limited to, databases (e.g., relational, object-oriented, etc.), file systems, flat files, distributed datastores in which data is stored on more than one node of a computer network, peer-to-peer network datastores, or the like.

The optional input/output (I/O) interface(s) 606 may facilitate the receipt of input information by the server 600 from one or more I/O devices as well as the output of information from the server 600 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; and so forth. Any of these components may be integrated into the server 600 or may be separate.

The server 600 may further include one or more network interface(s) 608 via which the server 600 may communicate with any of a variety of other systems, platforms, networks, devices, and so forth. The network interface(s) 608 may enable communication, for example, with one or more wireless routers, one or more host servers, one or more web servers, and the like via one or more of networks.

The antenna(s) 634 may include any suitable type of antenna depending, for example, on the communications protocols used to transmit or receive signals via the antenna(s) 634. Non-limiting examples of suitable antennas may include directional antennas, non-directional antennas, dipole antennas, folded dipole antennas, patch antennas, multiple-input multiple-output (MIMO) antennas, or the like. The antenna(s) 634 may be communicatively coupled to one or more transceivers 610 or radio components to which or from which signals may be transmitted or received. Antenna(s) 634 may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals including BLE signals, a Near Field Communication (NFC) antenna for transmitting or receiving NFC signals, a 900 MHz antenna, and so forth.

The transceiver(s) 610 may include any suitable radio component(s) for, in cooperation with the antenna(s) 634, transmitting or receiving radio frequency (RF) signals in the bandwidth and/or channels corresponding to the communications protocols utilized by the server 600 to communicate with other devices. The transceiver(s) 610 may include hardware, software, and/or firmware for modulating, transmitting, or receiving—potentially in cooperation with any of antenna(s) 634—communications signals according to any of the communications protocols discussed above including, but not limited to, one or more Wi-Fi and/or Wi-Fi direct protocols, as standardized by the IEEE 802.11 standards, one or more non-Wi-Fi protocols, or one or more cellular communications protocols or standards. The transceiver(s) 610 may further include hardware, firmware, or software for receiving GNSS signals. The transceiver(s) 610 may include any known receiver and baseband suitable for communicating via the communications protocols utilized by the server 600. The transceiver(s) 610 may further include a low noise amplifier (LNA), additional signal amplifiers, an analog-to-digital (A/D) converter, one or more buffers, a digital baseband, or the like.

Referring now to functionality supported by the various program module(s) depicted in FIG. 6, the implementation module(s) 626 may include computer-executable instructions, code, or the like that responsive to execution by one or more of the processor(s) 602 may perform functions including, but not limited to, overseeing coordination and interaction between one or more modules and computer executable instructions in data storage 620, determining user selected actions and tasks, determining actions associated with user interactions, determining actions associated with user input, initiating commands locally or at remote devices, and the like.

The style module(s) 627 may include computer-executable instructions, code, or the like that responsive to execution by one or more of the processor(s) 602 may perform functions including, but not limited to, analyzing and processing image data (e.g., still frames and/or video clips) and determining from the image data one or more style groups and/or representative image frames corresponding to a certain style.

The communication module(s) 628 may include computer-executable instructions, code, or the like that responsive to execution by one or more of the processor(s) 602 may perform functions including, but not limited to, communicating with one or more devices, for example, via wired or wireless communication, communicating with servers (e.g., remote servers), communicating with datastores and/or databases, communicating with imaging systems and/or analyst devices, sending or receiving notifications or commands/directives, communicating with cache memory data, communicating with computing devices, and the like.

The content module(s) 629 may include computer-executable instructions, code, or the like that responsive to execution by one or more of the processor(s) 602 may perform functions including, but not limited to, determining input images, processing input images, segmenting input images, and/or determining content in input images.

The style transfer module(s) 630 may include computer-executable instructions, code, or the like that responsive to execution by one or more of the processor(s) 602 may perform functions including, but not limited to processing input images and/or representative style images to generate styled input images, each incorporating a style from the representative style images.

The image analyzer module(s) 631 may include computer-executable instructions, code, or the like that responsive to execution by one or more of the processor(s) 602 may perform functions including, but not limited to processing the styled input images and detecting cardiovascular anomalies based on the styled input images and/or optionally determining or detecting standard views, anatomy keypoints, measurements, and/or performing segmentation based on the styled input images.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Program module(s), applications, or the like disclosed herein may include one or more software components, including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component including assembly language instructions may require conversion into executable machine code by an assembler prior to execution by the hardware architecture and/or platform.

Another example programming language may be a higher-level programming language that may be portable across multiple architectures. A software component including higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component including instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may include other custom-developed application software, operating system functionality (e.g., device drivers, data storage (e.g., file management) routines, other common routines, and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

It should be understood that any of the computer operations described herein above may be implemented at least in part as computer-readable instructions stored on a computer-readable memory. It will of course be understood that the embodiments described herein are illustrative, and components may be arranged, substituted, combined, and designed in a wide variety of different configurations, all of which are contemplated and fall within the scope of this disclosure.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method for determining a likelihood of a presence of one or more cardiovascular anomalies in a patient, the method comprising:
   determining a plurality of sets of image data corresponding to a plurality of style groups, each set of image data indicative of a portion of a sample patient's cardiovascular system and comprising a series of image frames;
   determining a plurality of representative sets of image data based on the plurality of sets of image data each comprising at least one representative image frame corresponding to one of the plurality of style groups;
   determining a first set of image data indicative of a first portion of the patient's cardiovascular system and comprising a first series of image frames;
   processing the first set of image data and each representative set of image data of the plurality of representative sets of image data using a style transfer generator to generate a set of styled image data for each representative set of image data; and
   processing each set of styled set of image data for each representative set of image data using an image analyzer to determine the likelihood of a presence of one or more cardiovascular anomalies for each set of styled image data.

2. The method of claim 1, further comprising:
   processing the plurality of sets of image data using a classification model to generate style data for each set of image data of the plurality of sets of image data, the style data corresponding to feature maps associated with each set of image data of the plurality of sets of image data;
   processing the style data using a clustering model to determine a plurality of style groups corresponding to the plurality of sets of image data.

3. The method of claim 1, wherein:
   the first set of image data is generated by a first imaging system corresponding to a first imaging system type;
   the plurality of sets of image data comprise a second set of image data generated by a second imaging system corresponding to a second imaging system type, and
   the first imaging system type is different than the second imaging system type.

4. The method of claim 3, wherein the first imaging system comprises a first imaging sensor corresponding to a first imaging sensor type and the second imaging system comprises a second imaging sensor corresponding to a second imaging sensor type, the first imagining sensor type being a different from the second imaging sensor type.

5. The method of claim 1, wherein determining a plurality of representative sets of image data comprises using one or more of a Akaike Information Criterion (AIC) and a Bayesian Information Criterion (BIC).

6. The method of claim 1, wherein the first set of image data comprises one or more video clips having sequential image frames.

7. The method of claim 6, wherein the first set of image data comprises a first image frame and a second image frame arranged immediately after the first image frame, and wherein processing the first set of image data and each representative set of image data of the plurality of representative sets of image data using the style transfer generator further comprises determining optical flow data based on the first image frame and the second image frame.

8. The method of claim 7, further comprising determining at least one constrained region in the second image frame based on the optical flow data.

9. The method of claim 1, wherein the style transfer generator is a convolutional neural network.

10. The method of claim 1, wherein the style transfer generator is a recurrent neural network comprising an encoder-decoder portion and a multi-instance normalization portion, the recurrent neural network being a spatiotemporal neural network.

11. The system of claim 1, wherein the style transfer generator is a convolutional neural network.

12. The system of claim 1, wherein the style transfer generator is a recurrent neural network comprising an encoder-decoder portion and a multi-instance normalization portion, the recurrent neural network being a spatiotemporal neural network.

13. A system for determining a likelihood of a presence of one or more cardiovascular anomalies in a patient, the system comprising:
   memory configured to store computer-executable instructions; and
   at least one computer processor configured to access memory and execute the computer-executable instructions to:
      determine a plurality of sets of image data corresponding to a plurality of style groups, each set of image data indicative of a portion of a sample patient's cardiovascular system and comprising a series of image frames;
      determine a plurality of representative sets of image data based on the plurality of sets of image data each comprising at least one representative image frame corresponding to one of the plurality of style groups;
      determine a first set of image data indicative of a first portion of the patient's cardiovascular system and comprising a first series of image frames;
      process the first set of image data and each representative set of image data of the plurality of representative sets of image data using the style transfer generator to generate a set of styled image data corresponding to each representative set of image data; and process the styled set of image data using an image analyzer to determine the likelihood of a presence of one or more cardiovascular anomalies in the set of styled image data.

14. The system of claim 13, wherein the computer processor is further configured to execute the computer-executable instructions to:
process the plurality of sets of image data using a classification model to generate style data for each set of image data of the plurality of sets of image data, the style data corresponding to feature maps associated with each set of image data of the plurality of sets of image data; and
process the style data using a clustering model to determine a plurality of style groups corresponding to the plurality of sets of image data.

15. The system of claim 13, wherein:
the first set of image data is generated by a first imaging system corresponding to a first imaging system type;
the plurality of sets of image data comprise a second set of image data generated by a second imaging system corresponding to a second imaging system type, and
the first imaging system type is different than the second imaging system type.

16. The system of claim 15, wherein the first imaging system comprises a first imaging sensor corresponding to a first imaging sensor type and the second imaging system comprises a second imaging sensor corresponding to a second imaging sensor type, the first imagining sensor type being a different from the second imaging sensor type.

17. The system of claim 13, wherein determining a plurality of representative sets of image data comprises using one or more of a Akaike Information Criterion (AIC) and a Bayesian Information Criterion (BIC).

18. The system of claim 13, wherein the first set of image data comprises one or more video clips having sequential image frames.

19. The system of claim 18, wherein the first set of image data comprises a first image frame and a second image frame arranged immediately after the first image frame, and wherein processing the first set of image data and each representative set of image data of the plurality of representative sets of image data using the style transfer generator further comprises determining optical flow data based on the first image frame and the second image frame.

20. The system of claim 19, wherein the computer processor is further configured to execute the computer-executable instructions to determine at least one constrained region in the second image frame based on the optical flow data.

21. A method for determining a likelihood of a presence of one or more cardiovascular anomalies in a patient, the method comprising:
determining a plurality of sets of image data corresponding to a plurality of style groups;
determining representative image data corresponding to a representative style group;
processing the plurality of sets of image data and the representative image data using a style transfer generator to generate a set of styled image data corresponding to the representative style group;
training an image analyzer using the set of styled image data to determine the likelihood of a presence of one or more cardiovascular anomalies;
determining a set of patient image data indicative of a portion of the patient's cardiovascular system; and
processing the set of patient image data and the representative image data using a style transfer generator to generate a set of styled patient image data corresponding to the representative style group.

22. The method of claim 21, further comprising processing the set of styled patient image data using the image analyzer to determine the likelihood of a presence of one or more cardiovascular anomalies present in the set of styled patient image data.

23. The method of claim 21, wherein:
the set of patient image data is generated by a first imaging system corresponding to a first imaging system type;
the plurality of sets of image data comprise a second set of image data generated by a second imaging system corresponding to a second imaging system type, and
the first imaging system type is different than the second imaging system type.

24. The method of claim 23, wherein the first imaging system comprises a first imaging sensor corresponding to a first imaging sensor type and the second imaging system comprises a second imaging sensor corresponding to a second imaging sensor type, the first imagining sensor type being a different from the second imaging sensor type.

25. The method of claim 21, wherein the set of patient image data comprises one or more video clips having sequential image frames.

26. The method of claim 21, wherein the set of patient image data comprises a first image frame and a second image frame arranged immediately after the first image frame, and wherein processing the set of patient image data using the style transfer generator further comprises determining optical flow data based on the first image frame and the second image frame.

27. The method of claim 26, further comprising determining at least one constrained region in the second image frame based on the optical flow data.

28. The method of claim 21, wherein the style transfer generator is a convolutional neural network.

29. The method of claim 21, wherein the style transfer generator is a recurrent neural network comprising an encoder-decoder portion and a multi-instance normalization portion, the recurrent neural network being a spatiotemporal neural network.

30. The method of claim 21, wherein the representative image data comprises a representative image frame.

* * * * *